(12) United States Patent
Wallingford et al.

(10) Patent No.: US 8,049,877 B2
(45) Date of Patent: Nov. 1, 2011

(54) COMPUTER-IMPLEMENTED METHODS, CARRIER MEDIA, AND SYSTEMS FOR SELECTING POLARIZATION SETTINGS FOR AN INSPECTION SYSTEM

(75) Inventors: Richard Wallingford, San Jose, CA (US); Stephanie Chen, Fremont, CA (US); Jason Kirkwood, Santa Clara, CA (US); Tao Luo, Fremont, CA (US); Yong Zhang, Cupertino, CA (US); Lisheng Gao, Morgan Hill, CA (US)

(73) Assignee: KLA-Tencor Corp., San Jose, CA (US)

( * ) Notice: Subject to any disclaimer, the term of this patent is extended or adjusted under 35 U.S.C. 154(b) by 840 days.

(21) Appl. No.: 12/120,577

(22) Filed: May 14, 2008

(65) Prior Publication Data

US 2009/0284733 A1    Nov. 19, 2009

(51) Int. Cl.
*G01N 21/00* (2006.01)
(52) U.S. Cl. ..................... 356/237.2; 356/364
(58) Field of Classification Search .... 356/237.2–237.6, 356/364–370
See application file for complete search history.

(56) References Cited

FOREIGN PATENT DOCUMENTS

| JP | 2000155099 | 6/2000 |
|----|------------|--------|
| JP | 2003287504 | 10/2003 |
| JP | 2005189113 | 7/2005 |
| JP | 2007213016 | 8/2007 |
| KR | 10-2006-0048960 | 5/2006 |

OTHER PUBLICATIONS

International Preliminary Report on Patentability for PCT/US2009/043825 mailed Nov. 25, 2010.
Written Opinion and International Search Report for PCT/US2009/043825, mailed Nov. 24, 2009.

*Primary Examiner* — Tarifur Chowdhury
*Assistant Examiner* — Tara S Pajoohi
(74) *Attorney, Agent, or Firm* — Ann Marie Mewherter (57) ABSTRACT

Computer-implemented methods, carrier media, and systems for selecting polarization settings for an inspection system for inspection of a layer of a wafer are provided. One method includes detecting a population of defects on the layer of the wafer using results of each of two or more scans of the wafer performed with different combinations of polarization settings of the inspection system for illumination and collection of light scattered from the wafer. The method also includes identifying a subpopulation of the defects for each of the different combinations, each of which includes the defects that are common to at least two of the different combinations, and determining a characteristic of a measure of signal-to-noise for each of the subpopulations. The method further includes selecting the polarization settings for the illumination and the collection to be used for the inspection corresponding to the subpopulation having the best value for the characteristic.

21 Claims, 2 Drawing Sheets

COMPUTER-IMPLEMENTED METHODS, CARRIER MEDIA, AND SYSTEMS FOR SELECTING POLARIZATION SETTINGS FOR AN INSPECTION SYSTEM

BACKGROUND OF THE INVENTION

1. Field of the Invention

This invention generally relates to computer-implemented methods, carrier media, and systems for selecting polarization settings for an inspection system for inspection of a layer of a wafer. Certain embodiments relate to a computer-implemented method for determining a characteristic of a measure of signal-to-noise for subpopulations of defects, each of which includes defects that are common to at least two different combinations of polarization settings of the inspection system, and selecting the polarization settings for illumination and collection to be used for inspection of a layer of a wafer corresponding to the subpopulation having the best value for the characteristic.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Inspection for many different types of defects has also become more important recently. For instance, in order to use the inspection results to monitor and correct semiconductor fabrication processes, it is often necessary to know what types of defects are present on a specimen. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Many different types of inspection systems have been developed to detect the different types of defects described above. In addition, most inspection systems are configured to detect multiple different types of defects. In some instances, a system that is configured to detect different types of defects may have adjustable image acquisition and sensitivity parameters such that different parameters can be used to detect different defects or avoid sources of unwanted (nuisance) events. For instance, the spot or pixel size, polarization or the algorithm settings for the angles of collection may be different for an inspection process used to detect particulate defects than for an inspection process used to detect scratches.

Although an inspection system that has adjustable image acquisition and sensitivity parameters presents significant advantages to a semiconductor device manufacturer, these inspection systems are useless if incorrect image acquisition and sensitivity parameters are used for an inspection process. For example, incorrect or non-optimized image acquisition and sensitivity parameters may produce such high levels of noise that no defects can be detected in the generated inspection data. In addition, since the detects, process conditions and noise on a specimen such as a reticle and a wafer may vary dramatically (and since the characteristics of the specimen itself may vary dramatically), the best image acquisition and sensitivity parameters for detecting the defects on a particular specimen may be difficult, if not impossible, to predict. Therefore, although using the correct image acquisition and sensitivity parameters will have a dramatic effect on the results of inspection, it is conceivable that many inspection processes are currently being performed with incorrect or non-optimized image acquisition and sensitivity parameters.

The task of setting up an inspection process for a particular specimen and a particular defect of interest may be extremely difficult for a user particularly when an inspection system has a relatively large number of adjustable image acquisition settings and sensitivity parameters. In addition, it may be impossible to know whether the best inspection process has been found unless all possible combinations of the image acquisition parameters have been tested. However, most inspection processes are currently set up using a large number of manual processes (e.g., manually setting the image acquisition parameters, manually analyzing the resulting inspection data, etc.). As such, setting up the inspection process may take a relatively long time. Furthermore, depending on the types of specimens that will be inspected with the inspection system, a different inspection process may need to be set up for each different type of specimen. Obviously, therefore, setting up the inspection processes for all of the different specimens that are to be inspected may take a prohibitively long time.

Previous methods for selecting one or more polarization settings for an inspection recipe for a process layer are labor intensive processes, which include several iterative steps. The first step of one such method is to perform an inspection scan with predefined default settings for a dark field inspection system. The goal of this step is to locate defects (or anomalies) on the surface of the wafer for the process layer of interest. Of this entire population of defects, the user manually selects a sub-sample of defects to examine further. For each defect, a signal-to-noise ratio is determined (based on the raw image intensities). Basically, this signal-to-noise ratio is a measure of how much more intense the defect scatters relative to its background (or non-defective region). The signal-to-noise for a given defect is strongly dependent on the polarization choice. Therefore, the user must cycle through all of the available polarization options on the dark field inspection system and determine which polarization state will maximize the overall signal-to-noise for this subset of defects.

There are, however, a number of disadvantages to such methods. For example, such methods can be substantially time-consuming and tedious. Depending on the nature of the process layer, the methods described above can take anywhere from a few hours to a few days to find the best polarization setting. In addition, if the user has no prior knowledge of the process layer, the user may choose non-interesting defects in the sub-sample and as a result choose an incorrect polarization setting for the actual defects of interest.

Accordingly, it would be advantageous to develop computer-implemented methods, carrier media, and/or systems for selecting polarization settings for an inspection system for inspection of a layer of a wafer that are less labor intensive, quicker, and less tedious than previously used methods and that result in polarization setting selections that are more appropriates or even optimal, for inspection of a layer on a wafer than polarization settings selected using the methods described above.

SUMMARY OF THE INVENTION

The following description of various embodiments of computer-implemented methods, carrier media, and systems is not to be construed in any way as limiting the subject matter of the appended claims.

One embodiment relates to a computer-implemented method for selecting polarization settings for an inspection system for inspection of a layer of a wafer. The method includes detecting a population of defects on the layer of the wafer using results of each of two or more scans of the wafer performed with different combinations of polarization settings of the inspection system for illumination and collection of light scattered from the wafer. The method also includes identifying a subpopulation of the defects for each of the different combinations. Each of the subpopulations includes the defects that are common to at least two of the different combinations. In addition, the method includes determining a characteristic of a measure of signal-to-noise for each of the subpopulations. The method further includes selecting the polarization settings for the illumination and the collection to be used for the inspection of the layer of the wafer corresponding to the subpopulation having the best value for the characteristic.

In one embodiment, each of the two or more scans includes a scan of only a portion of the wafer. In another embodiment, the detecting step includes applying a single parameter threshold to the results of each of the two or more scans. In one such embodiment, the measure of the signal-to-noise includes results of the applying step. In an additional embodiment, all steps of the method are performed without knowledge of defects of interest on the wafer. In a further embodiment, all steps of the method are performed without identifying defects of interest on the wafer.

In one embodiment, the defects that are common to the at least two of the different combinations include defects that have a higher probability of being salient defects than defects that are not common to the at least two of the different combinations. In another embodiment, the different combinations include all combinations of the polarization settings for the illumination and the collection available on the inspection system. In an additional embodiment, the characteristic of the measure of the signal-to-noise includes an average. In one such embodiment, the best value includes the highest value for the average.

In one embodiment, the selecting step includes selecting one or more polarization settings for the illumination prior to selecting one or more polarization settings for the collection. In another embodiment, the selecting step includes selecting one or more polarization settings for the illumination and selecting one or more polarization settings for the collection based on the subpopulations corresponding to the one or more polarization settings selected for the illumination.

In one embodiment, the selecting step includes selecting one or more polarization settings for the illumination using a first subset of the subpopulations and selecting one or more polarization settings for the collection using a second subset of the subpopulations. In one such embodiment, the first subset includes the subpopulations that include the defects that are common to the at least two of the different combinations of all of the polarization settings for the illumination and only one of the polarization settings for the collection. In another such embodiment, the second subset includes the subpopulations that include the defects that are common to the at least two of the different combinations of the polarization setting selected for the illumination and all of the polarization settings available for the collection.

In one embodiment, the inspection system includes one or more illumination channels, and the selecting step includes selecting at least one polarization setting for at least one of the one or more illumination channels. In another embodiment, the inspection system includes two or more collection channels, and the selecting step includes selecting the polarization setting for at least two of the two or more collection channels.

In one embodiment, the inspection system includes more than one collection channel. In one such embodiment, the selecting step includes selecting the polarization settings for the collection such that the polarization settings selected for at least two of the more than one collection channel are the same. In another such embodiment, the selecting step includes selecting the polarization settings for at least two of the more than one collection channel independently.

In one embodiment, the method is performed for different layers on the wafer. In another embodiment, all steps of the method are performed without user intervention.

Each of the steps of the method described above may be performed as described further herein. In addition, each of the embodiments of the method described above may include any other step(s) of any other method(s) described herein. Furthermore, each of the embodiments of the method described above may be performed by any of the systems described herein.

Another embodiment relates to a carrier medium that includes program instructions executable on a computer system for performing a computer-implemented method for selecting polarization settings for an inspection system for inspection of a layer on a wafer. The computer-implemented method includes detecting a population of defects on the layer of the wafer using results of each of two or more scans of the wafer performed with different combinations of polarization settings of the inspection system for illumination and collection of light scattered from the wafer. The method also includes identifying a subpopulation of the defects for each of the different combinations. Each of the subpopulations includes the defects that are common to at least two of the different combinations. In addition, the method includes determining a characteristic of a measure of signal-to-noise for each of the subpopulations. The method further includes selecting the polarization settings for the illumination and the collection to be used for the inspection of the layer of the wafer corresponding to the subpopulation having the best value for the characteristic.

The carrier medium described above may be further configured as described herein. The steps of the computer-implemented method may be performed as described further herein. In addition, the computer-implemented method for which the program instructions are executable may include any other step(s) of any other method(s) described herein.

An additional embodiment relates to a system configured to select polarization settings for inspection of a layer of a wafer. The system includes an inspection system configured to generate output by performing two or more scans of the wafer with different combinations of polarization settings for illumination and collection of light scattered from the wafer. The system also includes a computer system configured to detect a population of defects on the wafer using the output generated by each of the two or more scans. The computer system is also configured to identify a subpopulation of the defects for each of the different combinations. Each of the subpopulations includes the defects that are common to at least two of the different combinations. In addition, the computer system is configured to determine a characteristic of a measure of signal-to-noise for each of the subpopulations. The computer system is further configured to select the polarization settings for the illumination and the collection to be used for the inspection of the layer of the wafer corresponding to the subpopulation having the best value for the characteristic. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device know in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
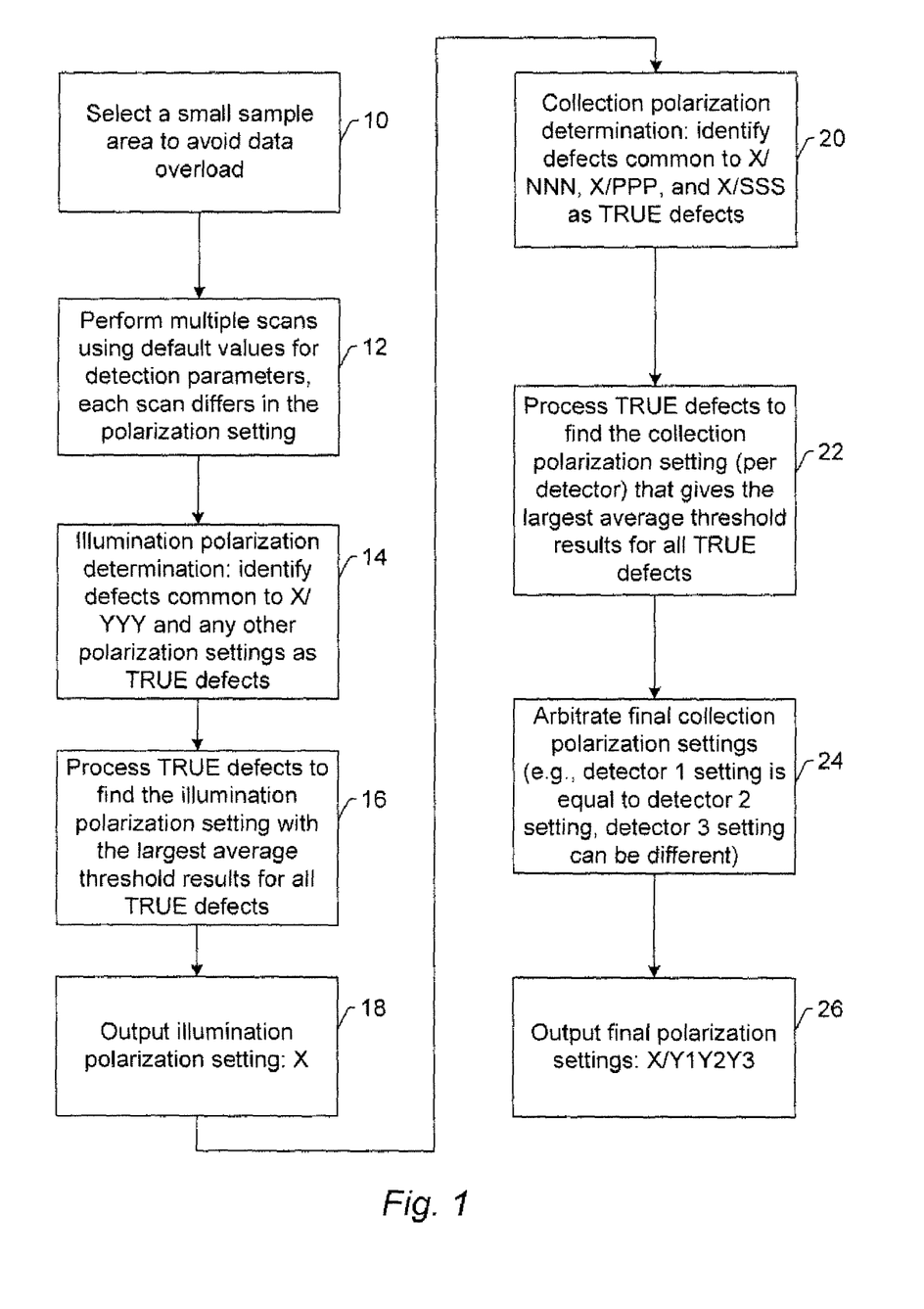
FIG. 1 is a flow chart illustrating one embodiment of a computer-implemented method for selecting polarization settings for an inspection system for inspection of a layer of a wafer.

One embodiment relates to a computer-implemented method for selecting polarization settings for an inspection system for inspection of a layer of a wafer. One embodiment of such a computer-implemented method is shown in FIG. 1. It is noted that the steps shown in FIG. 1 are not essential to practice of the method. One or more steps may be omitted or added to the method illustrated in FIG. 1, and the method can still be practiced within the scope of these embodiments.

In one embodiment, the inspection system includes a dark field inspection system. The dark field inspection system may be configured as described further herein. In addition, in some embodiments, all steps of the method are performed without user intervention. For example, all steps of the method described herein may be performed automatically. Therefore, the methods described herein may be fully automated processes. In this manner, the embodiments described herein may be used for automatic polarization setting selection for dark field inspection systems. In particular, the embodiments described herein can be used to select an optimal polarization setting for any given process layer (of the semiconductor manufacturing process) without any user interaction on a dark field inspection system. Therefore, the embodiments described herein can improve ease of use for the dark field inspection system by significantly reducing the setup time. With the optimal polarization setting setup, the signal-to-noise ratio for a given process layer can be considerably enhanced, and thus the dark field inspection sensitivity can be greatly improved. This method can also be configured to have user input to improve the performance of polarization selections.

In one embodiment, each of the two or more scans described further herein includes a scan of only a portion of the wafer. For example, for a given process layer, multiple inspection scans may be performed on a relatively small sample area of the layer on the wafer. The relatively small sample area may include, for example, the area of a die on the wafer such as a die that is centrally located on the wafer. However, the relatively small sample area may include any other suitable sample area on the wafer. For example, the relatively small sample area may be selected such that a suitable number of defects are detected in the embodiments described herein without unnecessarily increasing the time in which the results that are generated by each of the two or more scans can be processed. The method may include selecting the small sample area. For example, as shown in step 10 of FIG. 1 the method may include selecting a small sample area to avoid data overload. The portion of the wafer that is scanned in each of the scans may include the same portion of the wafer. In other words, each of the scans may be performed on the same area of the wafer. In this manner, the defects that are detected using the results of each of the two or more scans as described further herein may be determined more accurately than if different scans are performed on different areas of the wafer in which different defects would be located. Each of the scans may be performed in any suitable manner. In addition, the combinations of polarization settings used for the scans may be altered between the scans in any suitable manner.

The method includes detecting a population of defects on the layer of the wafer using the results of each of the two or more scans of the wafer performed with different combinations of polarization settings of the inspection system for illumination and collection of light scattered from the wafer. Therefore, for a given process layer, multiple inspection scans are performed. For example, as shown in step 12 of FIG. 1, the method may include performing multiple scans using default values for detection parameters, and each scan differs in the polarization setting. However, the embodiments described herein may or may not include performing the two or more scans of the wafer with the different combinations of polarization settings. For example, the embodiments described herein may include acquiring the results of each of the two or more scans of the wafer from an inspection system that performed each of the two or more scans or from a storage medium (e.g., a storage medium of the inspection system, a fab database, etc.) in which the inspection system stored the results of each of the two or more scans.

In one embodiment, the different combinations include all combinations of the polarization settings for the illumination and the collection available on the inspection system. For example, each of the scans may differ in the choice of polarization setting, until all polarization setting choices have been used. The different combinations of the polarization settings are combinations of illumination and collection polarization settings. In one particular example, if there are nine different combinations for polarization setting choices on a dark field inspection system, the method may include performing nine different scans, one for each of the different combinations. For example, dark field inspection system architecture may include three collectors (or detectors), each allowing an independent polarization setting. Thus, an example of a combination of polarization settings would be $X/Y_1Y_2Y_3$, where X is the illumination polarization setting (e.g., either p-polarized (P), s-polarized (S), or circularly polarized (C)), and $Y_1$, $Y_2$, and $Y_3$ are the collection polarization settings for each of the three detectors, respectively. Options for the collection polarization settings may be, for example, S, P, or non-polarized (N). In this manner, each scan described above may be performed using different combinations of the polarization settings to cycle through all possible combinations.

In one embodiment, the detecting step includes applying a single parameter threshold to the results of each of the two or more scans. For example, the embodiments described herein may use a single parameter inspection algorithm to detect defects during an inspection scan of the process layer. Detecting the population of defects for each of the scans may be performed using a default setting for the detection threshold to determine the entire defect population. The setting for the detection threshold determines the aggressiveness with which defects will be detected. The default setting may be selected to be substantially close to but above the noise floor of the results of each of the two or more scans. In this manner, multiple scans may be performed using a default value for the detection threshold. The defects may also be determined using any suitable comparison known in the art such as a cell-to-cell comparison.

The method also includes identifying a subpopulation of the defects for each of the different combinations. Each of the subpopulations includes the defects that are common to at least two of the different combinations. In one embodiment, the defects that are common to the at least two of the different combinations include defects that have a higher probability of being salient defects than defects that are not common to the at least two of the different combinations. For example, an unsupervised classification method can be used to automatically classify each defect as either TRUE or FALSE. The classification is based on the probability of each defect being captured by multiple polarization settings. In particular, the TRUE defects may be defined as defects that are captured by at least two of the scans performed using different combinations of the polarization settings. Therefore, TRUE defects are effectively those defects that show some correlation from one scan to another. In this manner, the TRUE defects have a higher probability of being captured by two or more polarization settings than the FALSE defects. As such, unsupervised classification is based on the fact that TRUE defects have a relatively high probability of being captured with two or more polarization settings while FALSE defects have a relatively low probability of being captured using multiple polarization settings.

In an additional embodiment, all steps of the method are performed without knowledge of defects of interest on the wafer. In a further embodiment, all steps of the method are performed without identifying defects of interest on the wafer. In other words, the subpopulations of the defects are identified as described further herein regardless of whether or not the defects included in the subpopulations are defects of interest. Instead, by identifying defects that are detected by two or more of the polarization setting combinations at which the scans are performed, the defects that are included in the subpopulations are most likely salient defects as opposed to nuisance defects or noise. Therefore, the polarization settings for illumination and collection can be selected as described herein based on the subpopulations, a substantial portion of which include salient defects instead of nuisance defects or noise. As such, the polarization settings for the illumination and the collection can be determined substantially accurately without identifying or finding defects of interest on the layer of the wafer.

In contrast, in previously used methods, a user may perform a quick scan of the wafer, then review some of the defects detected using results of the quick scan. The user may then use the results of the review to identify at least some defects of interest on the layer. An additional scan or additional scans may then be performed at different polarization settings to grab images of the identified defects of interest. The images may then be processed to determine the intensity of the defects in the images versus the intensity of the background in the images to measure the signal-to-noise ratio of the defects detected using different polarization settings. The images of defects of interest are used in this method to ensure that the polarization settings that are selected based on the images and the signal-to-noise ratio determined using the images are appropriate for detecting defects of interest on the layer of the wafer. Otherwise, polarization settings that increase the detection of nuisance defects may be inadvertently selected for use for inspection of the layer of the wafer, which is disadvantageous for obvious reasons.

In order to perform such methods, therefore, the user must not only identify defects of interest using the results of the review, which may take a substantially long time particularly if the quick scan is performed with polarization settings that result in substantial nuisance detection or noise or that reduce the detection of defects of interest, but also must have some knowledge about the defects of interest, which may not always be available to the user. In this manner, if the user selects defects for which images are to be grabbed that are not defects of interest, the polarization settings that are selected based on measurements performed on such images may produce polarization settings that are suboptimal for detecting the true defects of interest. Therefore, since the embodiments described herein can be performed without knowledge of the defects of interest, the embodiments described herein can be used to determine polarization settings quicker than previously used methods and regardless of whether knowledge about the defects of interest is available. In addition, the polarization settings that are selected using the embodiments described herein may be more optimal for detecting defects of interest than polarization settings selected using previously used methods even though knowledge of the defects of interest is not used in the embodiments described herein.

The method also includes determining a characteristic of a measure of signal-to-noise for each of the subpopulations, in one embodiment, as described above, the detecting step includes applying a single parameter threshold to the results of each of the two or more scans. In one such embodiment, the measure of the signal-to-noise includes results of the applying step. For example, as described above, the embodiments described herein may use a single parameter inspection algorithm to detect defects during an inspection scan of the process layer. In such embodiments, the reported detection threshold value for each defect may be used as a measure of signal-to-noise in the embodiments described herein rather than the intensity values from a raw image scan. For example, in general, the single parameter detection algorithm applies a single threshold value determined based on the average noise to produce a value for the defect. Higher values indicate that the defect "stands out" more from the background of the image. Therefore, the detection attribute from each defect that is compared against a threshold is a direct and robust measure of signal-to-noise. As such, the defect's resulting thresholded value directly corresponds to detectability of the defect. The measure of the signal-to-noise may be determined using any other suitable algorithm known in the art. In an additional embodiment, the characteristic of the measure of the signal-to-noise includes an average. The average of the measure of the signal-to-noise for each subpopulation of defects may be determined in any suitable manner.

The method further includes selecting the polarization settings for the illumination and the collection to be used for the inspection of the layer of the wafer corresponding to the subpopulation having the best value for the characteristic. For example, as described above, in one embodiment, the characteristic of the measure of the signal-to-noise includes an average. In one such embodiment, the best value includes the highest value for the average. For example, once the TRUE and FALSE defect subpopulations are identified as described herein, the method may then include determining the polarization setting with the highest average detection threshold value for the TRUE subpopulation of defects. In this manner, the defects that are automatically classified as being TRUE defects are further processed to determine the polarization setting that maximizes a characteristic of a measure of signal-to-noise for the defects. In this manner, the polarization settings corresponding to the subpopulation for which the highest average signal-to-noise is determined may be selected thereby providing the best polarization settings for achieving the highest signal-to-noise ratio for inspection of the layer on the wafer.

In some embodiments, selecting the polarization settings may include weighting one or more of the different combinations of the polarization settings. For example, different combinations of the polarization settings that are used more often may be given a larger weight than combinations of the polarization settings that are used less often. The different combinations of polarization settings may be weighted by applying a weight to the characteristic of the measure of the signal-to-noise determined for each subpopulation corresponding to one of the different combinations. Such weighting of the characteristic corresponding to the different subpopulations may be performed for selecting the polarization setting for both illumination and collection.

As described above, the area of the wafer that is scanned in each of the two or more scans may include a relatively small area of the wafer. The area of the wafer that is scanned may also include different regions of the layer formed on the wafer. For example, the area of the wafer that is scanned may include array regions and logic regions. In some such examples, the results of each of the two or more scans that are used in the embodiments described herein may include the results for only one region in the area of the wafer that is scanned or more than one region in the area of the wafer that is scanned. For example, if the area of the wafer that is scanned includes both array regions and logic regions, the results of each of the two or more scans that are used in the embodiments described herein may include the results for only the array region the results for only the logic region, or the results for both the array region and the logic region. The results of each of the two or more scans of the area on the wafer that correspond to different regions in the area may be identified in any suitable manner.

Using the results for only one of the regions included in the area of the wafer that is scanned may result in polarization setting selections that are optimized for only that one region on the wafer. The results for the regions included in the scanned area of the wafer that are used in the embodiments described herein may, therefore, be selected based on the regions of interest and may be selected by a user. In addition, using the results for different regions included in the area on the wafer that is scanned may result in different polarization setting selections. For example, the measure of the signal-to-noise determined as described herein may be different for different regions in the area thereby resulting in different polarization setting selections based on the characteristic of the different measures of the signal-to-noise. In one particular example, the detection threshold results determined for different regions of the wafer may be different. In such examples, the detection threshold results determined for different regions may be normalized and/or weighted such that the polarization settings are optimized for more than one of the different regions or only one of the different regions.

In one embodiment, the selecting step includes selecting one or more polarization settings for the illumination prior to selecting one or more polarization settings for the collection. For example, the method may be divided into two phases: determination of the illumination polarization setting, then determining the collection polarization setting(s). In one such example, as shown in FIG. 1, illumination (or incident) polarization determination may include steps 14, 16, and 18, and collection polarization determination may include steps 20, 22, and 24. The illumination and collection polarization settings may be determined in the two phases as described further herein. For example, as shown in step 14 of FIG. 1, incident polarization determination may include identifying defects that are common to X/YYY and any other polarization settings as TRUE defects. In one such example, the defects that are common to X/NNN and any other polarization settings are classified as TRUE, where X is either S, P, or C. The common defects may be determined as described further herein.

As shown in step 16 of FIG. 1, illumination polarization determination may also include processing the TRUE defects to find the illumination polarization setting with the largest average threshold results for all TRUE defects. Processing the TRUE defects in this step may be performed as described further herein. Furthermore, as shown in step 18 of FIG. 1 illumination polarization determination may include outputting the illumination polarization setting: X. Outputting the illumination polarization setting may be performed in any suitable manner. For example, the determined illumination polarization setting may be stored as described further herein.

In another embodiment, the selecting step includes selecting one or more polarization settings for the illumination and selecting one or more polarization settings for the collection based on the subpopulations corresponding to the one or more polarization settings selected for the illumination. For example, as shown in FIG. 1, after the illumination polarization setting X is output in step 18, the method may include collection polarization determination steps 20, 22, and 24, which are performed based on the selected illumination polarization setting. In particular, as shown in step 20 of FIG. 1, collection polarization determination may include identifying the defects that are common to two or more of X/NNN, X/PPP, and X/SSS as TRUE defects, which may be performed as described herein. In this manner, defects that are common to any pair-wise combination of X/NNN, X/PPP, and X/SSS are classified as TRUE events. As such, the common defects may be determined based on the populations of defects that were detected using all possible combinations of the polarization setting selected for the illumination and all of the polarization settings available for the collection. Defects that are common to any two of the possible combinations are included in the subpopulations for both of the two combinations.

As shown in step 22 of FIG. 1, the collection polarization determination may include processing the TRUE defects to find the collection polarization setting (per detector) that gives the largest average threshold results for all TRUE defects, which may be performed as described herein. In addition, as shown in step 24 of FIG. 1, the collection polarization determination may include arbitrating the final collection polarization settings (e.g., such that detector 1 polarization setting is equal to detector 2 polarization setting, while detector 3 polarization setting can be different), which may be performed as described herein. The method shown in FIG. 1 may further include outputting the final polarization setting: $X/Y_1Y_2Y_3$, as shown in step 26. Outputting the final polarization settings may be performed in any suitable manner. For example, the determined final polarization settings may be stored as described further herein.

In one embodiment, the selecting step includes selecting one or more polarization settings for the illumination using a first subset of the subpopulations and selecting one or more polarization settings for the collection using a second subset of the subpopulations. For example, the method may include determining the illumination polarization setting using all of the available data, then revisiting a sub-sample of the data to determine the collection polarization setting(s). In this manner, a subset of the data used to determine the illumination polarization setting or settings may be used to determine the collection polarization settings. In one such embodiment, the first subset includes the subpopulations that include the defects that are common to the at least two of the different combinations of all of the polarization settings for the illumination and only one of the polarization settings for the collection. For example, for determination of the illumination polarization setting, TRUE defects identified as described above may be defined as those events that are common to the P/NNN combination of settings and any of the other combinations of settings, the S/NNN combination of settings and any of the other combination of settings, and the C/NNN combination of settings and any of the other combinations of settings.

In one example, a population of defects may be detected using the P/NNN combination of polarization settings. Another population of defects may be detected using the S/NNN combination of polarization settings, and an additional population of defects may be detected using the C/NNN combination of polarization settings. Therefore, "region A" of the populations may include defects that were detected by both the P/NNN combination of polarization settings and the S/NNN combination of polarization settings. "Region B" of the populations may include defects that were detected by both the S/NNN combination of polarization settings and the C/NNN combination of polarization settings. "Region C" of the populations may include defects that were detected by both the C/NNN combination of polarization settings and the P/NNN combination of polarization settings. "Region D" of the populations may include defects that were detected by all three combinations of polarization settings: P/NNN, S/NNN, and C/NNN. Therefore, the TRUE defects detected on the layer of the wafer include the defects included in regions A, B, C, and D. The numbers of defects that are included in each of the regions may be different.

The subpopulation of the defects for the P/NNN combination of polarization settings, therefore, includes defects included in regions A, C, and D. Therefore, the characteristic of the measure of signal-to-noise for the subpopulation corresponding to the P/NNN combination of polarization settings may be determined as described further herein based on the defects included in regions A, C, and D. The subpopulation of the defects for the S/NNN combination of polarization settings includes defects included in regions A, B, and D. Therefore, the characteristic of the measure of signal-to-noise for the subpopulation corresponding to the S/NNN combination of polarization settings may be determined as described further herein based on the defects included in regions A, B, and D. The subpopulation of the defects for the C/NNN combination of polarization settings includes defects included in regions B, C, and D. Therefore, the characteristic of the measure of signal-to-noise for the subpopulation corresponding to the C/NNN combination of polarization settings may be determined as described further herein based on the defects included in regions B, C, and D. Of these three subpopulations of TRUE defects, the subpopulation with the largest average detection threshold value determines the illumination polarization setting (e.g., either S, P, or C).

In another such embodiment, the second subset includes the subpopulations that include the defects that are common to at least two of the different combinations of the polarization setting selected for the illumination and all of the polarization settings available for the collection. For example, after the illumination polarization setting is chosen, determination of the collection polarization setting(s) may include revisiting the data to determine the collection polarization setting for each detector or channel independently. For example, if X is the selected illumination polarization setting, TRUE defects are now those defects that are common to any pair-wise combination of X/NNN, X/SSS, and X/PPP. Three subpopulations of defects are now identified for each detector.

In one example, a population of defects may be detected using the X/PPP combination of polarization settings. Another population of defects may be detected using the X/SSS combination of polarization settings, and an additional population of defects may be detected using the X/NNN combination of polarization settings. Therefore, "region E" of the populations may include defects that were detected by both the X/PPP combination of polarization settings and the X/SSS combination of polarization settings. "Region F" of the populations may include defects that were detected by both the X/SSS combination of polarization settings and the X/NNN combination of polarization settings. "Region G" of the populations may include defects that were detected by both the X/NNN combination of polarization settings and the X/PPP combination of polarization settings. "Region H" of the populations may include defects that were detected by all three combinations of polarization settings: X/PPP, X/SSS, and X/NNN. Therefore, the TRUE defects detected on the layer of the wafer include the defects included in regions E, F, G, and H. The numbers of defects that are included in each of the regions may be different.

The subpopulation of the defects for the X/PPP combination of polarization settings, therefore, includes defects included in regions A, G, and H. Therefore, the characteristic of the measure of signal-to-noise for the subpopulation corresponding to the X/PPP combination of polarization settings may be determined as described further herein based on the defects included in regions A, G, and H. The subpopulation of the defects for the X/SSS combination of polarization settings includes defects included in regions E, F, and H. Therefore, the characteristic of the measure of signal-to-noise for the subpopulation corresponding to the X/SSS combination of polarization settings may be determined as described further herein based on the defects included in regions E, F, and H. The subpopulation of the defects for the X/NNN combination of polarization settings includes defects included in regions F, G, and H. Therefore, the characteristic of the measure of signal-to-noise for the subpopulation corresponding to the X/NNN combination of polarization settings may be determined as described further herein based on the defects included in regions F, G, and H. Again, the population of TRUE defects with the largest average detection threshold value determines the collection polarization setting for a given detector.

In one embodiment, the inspection system includes one or more illumination channels, and the selecting step includes selecting at least one polarization setting for at least one of the one or more illumination channels. For example, if the system includes more than one illumination channel, the embodiments described herein may include selecting the polarization setting for one or more of the illumination channels (e.g., one of the illumination channels, some, but not all, of the illumination channels, or all of the illumination channels). The polarization setting for one or more (or each) of the illumination channels may be selected as described further herein. In addition, the polarization setting for one or more (or each) of the illumination channels may be selected independently.

In another embodiment, the inspection system includes two or more collection channels, and the selecting step includes selecting the polarization setting for at least two of the two or more collection channels. For example, if the system includes more than one collection channel, the embodiments described herein may include selecting the polarization setting for two or more of the collection channels (e.g., two of the collection channels, some, but not all, of the collection channels, or all of the collection channels). The polarization setting for one or more (or each) of the collection channels may be selected as described further herein. In addition, the polarization setting for one or more (or each) of the collection channels may be selected independently as described herein.

In one embodiment, the inspection system includes more than one collection channel. For example, the inspection system may be configured as described further herein. In one such embodiment, the selecting step includes selecting the polarization settings for the collection such that the polarization settings selected for at least two of the more than one collection channel are the same. For example, the method may include a final arbitration step to ensure that the collection polarization setting for a first detector (e.g., Detector 1) of the system matches that of a different detector (e.g., Detector 2) of the system. In one such example, the collection polarization setting for another detector (e.g., Detector 3) of the system may have no further arbitration. The polarization settings for detectors that generate output in similar manners (e.g., detectors that are symmetric) may be selected to be the same, while detectors that generate output in different manners (e.g., detectors that are not symmetric) may be selected to be different. In another such example, the polarization settings for channels of the inspection system that generate similar images may be selected to be the same.

In this manner, if different subpopulations are determined to have the best values for the characteristic for different collection channels, which image light similarly, then the values for the characteristic determined for more than one subpopulation may be used in combination to select the polarization settings for the different collection channels. For example, if collection channels 1 and 2 image light similarly, and subpopulations corresponding to different polarization settings are determined to have the best values of the characteristic for collection channels 1 and 2, then the method may include determining which one of the polarization settings resulted in the best overall value for the characteristic for both collection channels. In another such embodiment, the selecting step includes selecting the polarization settings for at least two of the more than one collection channel independently. For example, for inspection, all or some of the collection channels of an inspection system can have different polarization settings during inspection of the layer of the wafer.

In one embodiment, the method is performed for different layers on the wafer. For example, the method may be performed separately for different layers on the wafer. In this manner, different polarization settings for the illumination and the collection may be selected to be used for the inspection of the different layers on the wafer. The different layers on the wafer may be inspected using the same inspection system. In this manner, different polarization settings may be used with the same inspection system for inspection of different layers of the wafer. In addition, the different layers on the wafer may be inspected using different inspection systems. For example, the methods described herein may be performed for any inspection system based on knowledge about the different combinations of polarization settings that are available on the inspection system. In this manner, the polarization settings for inspection of each different layer on the wafer may be optimized using the embodiments described herein. As such, the polarization settings for inspection of each different layer on the wafer may be optimized thereby optimizing the signal-to-noise ratio and sensitivity of the inspection for each different layer using the embodiments described herein.

Each of the embodiments of the method described above may include any other step(s) of any other method(s)

described herein. Furthermore, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects the polarization settings, the method may include storing the polarization settings in an inspection recipe in a storage medium. Furthermore, the results may be stored "permanently," "semi-permanently," temporarily, or for some period of time. For example, the storage medium may be random access memory (RAM), and the results may not necessarily persist indefinitely in the storage medium.

The embodiments described herein have a number of advantages over other methods and systems for selecting polarization settings for an inspection system. For example, the embodiments described herein can be fully automated and eliminate the need for user intervention. The embodiments described herein can, therefore, be used to automate the previous manual and tedious process of polarization selection for dark field inspection thereby improving time to results and consistency in the inspection process. As such, the embodiments described herein can improve ease of use for the dark field inspection system by significantly reducing the setup time. The embodiments described herein can also be used to select optimal polarization settings for any given process layer (of the semiconductor manufacturing process) without any user interaction on a dark field inspection system. In addition, correct polarization setting selection is critical for the dark field inspection systems used to monitor the semiconductor manufacturing process since correct polarization settings maximize the signal-to-noise for the defects. In particular, with the optimal polarization setup, the signal-to-noise ratio for a given process layer can be considerably enhanced, and thus the dark field inspection sensitivity can be greatly improved. Therefore, with the correct polarization settings, the sensitivity of the inspection system is amplified thereby increasing the likelihood of capturing the defects of interest.

Figure 2:
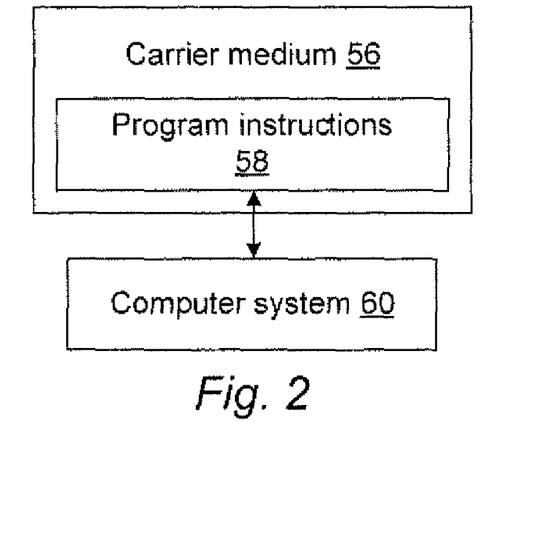
FIG. 2 is a block diagram illustrating one embodiment of a carrier medium that includes program instructions executable on a computer system for performing one or more of the computer-implemented methods described herein.

An additional embodiment relates to a carrier medium that includes program instructions executable on a computer system for performing a computer-implemented method for selecting polarization settings for an inspection system for inspection of a layer of a wafer. One such embodiment is shown in FIG. 2. In particular, as shown in FIG. 2, carrier medium 56 includes program instructions 58 executable on computer system 60.

The computer-implemented method includes detecting a population of defects on the layer of the wafer using results of each of two or more scans of the wafer performed with different combinations of polarization settings of the inspection system for illumination and collection of light scattered from the wafer. Detecting the populations of the defects may be performed as described herein. The method also includes identifying a subpopulation of the defects for each of the different combinations. Each of the subpopulations includes the defects that are common to at least two of the different combinations. Identifying the subpopulations may be performed as described herein. In addition, the method includes determining a characteristic of a measure of signal-to-noise for each of the subpopulations. Determining the characteristic of the measure of signal-to-noise may be performed as described further herein. The computer-implemented method further includes selecting the polarization settings for the illumination and the collection to be used for the inspection of the layer of the wafer corresponding to the subpopulation having the best value for the characteristic. Selecting the polarization settings for the illumination and the collection may be performed as described further herein. The computer-implemented method for which the program instructions are executable may include any other step(s) described herein.

Program instructions 58 implementing methods such as those described herein may be transmitted over or stored on carrier medium 56. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 3:
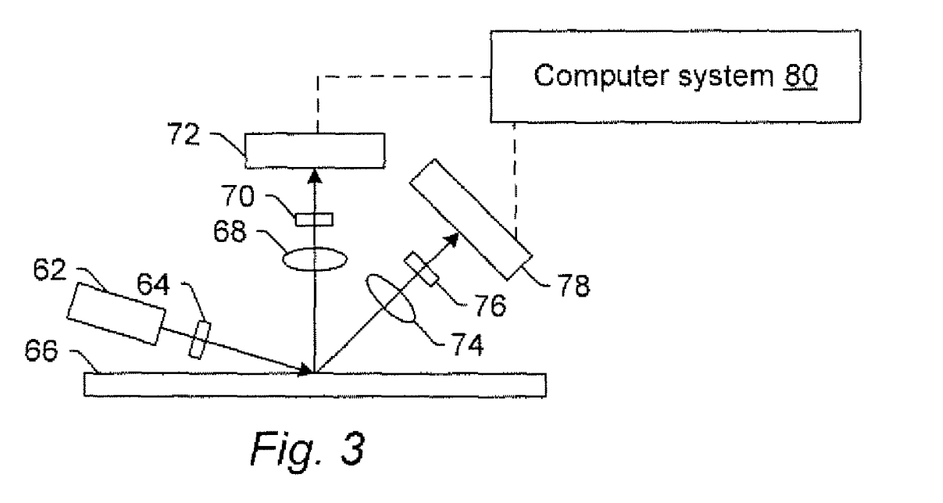
FIG. 3 is a schematic diagram illustrating a side view of a system configured to select polarization settings for inspection of a layer of a wafer.

Another embodiment relates to a system configured to select polarization settings for inspection of a layer of a wafer. One embodiment of such a system is shown in FIG. 3. The system includes an inspection system configured to generate output by performing two or more scans of the wafer with different combinations of polarization settings for illumination and collection of light scattered from the wafer. For example, as shown in FIG. 3, the inspection system includes light source 62. Light source 62 may include any suitable light source known in the art such as a laser. Light source 62 is configured to direct light to polarizing component 64, which may include any suitable polarizing component known in the art. In addition, the inspection system may include more than one polarizing component (not shown) each of which may be positioned independently in the path of the light from the light source. Each of the polarizing components may be configured to alter the polarization of the light from the light source in a different manner. The inspection system may be configured to move the polarizing components into and out of the path of the light from the light source in any suitable manner depending on which polarization setting is selected for illumination of the wafer during a scan or an inspection. The polarization setting used for the illumination of the wafer during a scan or inspection may be selected as described herein and may include any of the polarization settings described herein (e.g., P, S, and C).

Light exiting polarizing component 64 is directed to wafer 66 at an oblique angle of incidence, which may include any suitable oblique angle of incidence. The inspection system may also include one or more optical components (not shown) that are configured to direct light from light source 62 to polarizing component 64 or from polarizing component 64 to wafer 66. The optical components may include any suitable optical components known in the art such as, but not limited to, a reflective optical component. In addition, the light source, the polarizing component, and/or the one or more optical components may be configured to direct the light to the wafer at one or more angles of incidence (e.g., an oblique angle of incidence and/or a substantially normal angle of incidence). The inspection system may be configured to perform each of the scans by scanning the light over the wafer in any suitable manner.

Light scattered from wafer 66 may be collected and detected by multiple channels of the inspection system during each of the scans and during inspection. For example, light scattered from wafer 66 at angles relatively close to normal may be collected by lens 68. Lens 68 may include a refractive optical element as shown in FIG. 3, In addition, lens 68 may include one or more refractive optical elements and/or one or more reflective optical elements. Light collected by lens 68 may be directed to polarizing component 70, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 68 during a scan or an inspection. The polarization setting used for the detection of the light collected by lens 68 during a scan or inspection may be selected as described herein and may include any of the polarization settings described herein (e.g., P, S, and N).

Light exiting polarizing component 70 is directed to detector 72. Detector 72 may include any suitable detector known in the art such as a charge coupled device (CCD) or another type of imaging detector. Detector 72 is configured to generate output that is responsive to the scattered light collected by lens 68 and transmitted by polarizing component 70 if positioned in the path of the collected scattered light. Therefore, lens 68, polarizing component 70 if positioned in the path of the light collected by lens 68, and detector 72 form one channel of the inspection system. This channel of the inspection system may include any other suitable optical components (not shown) known in the art such as a Fourier filtering component.

Light scattered from wafer 66 at different angles may be collected by lens 74. Lens 74 may be configured as described above. Light collected by lens 74 may be directed to polarizing component 76, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner, The inspection system may be configured to move the polarizing components into and out of the path of the light collected by the lens in any suitable manner depending on which polarization setting is selected for detection of the light collected by lens 74 during a scan or an inspection. The polarization setting used for detection of the light collected by lens 74 during a scan or inspection may be selected as described herein and may include any of the polarization settings described herein (e.g., P, S, and N).

Light exiting polarizing component 76 is directed to detector 78, which may be configured as described above. Detector 78 is also configured to generate output that is responsive to the collected scattered light that passes through polarizing component 76 if positioned in the path of the scattered light. Therefore, lens 74, polarizing component 76 if positioned in the path of the light collected by lens 74, and detector 78 may form another channel of the inspection system. This channel may also include any other optical components (not shown) described above. In some embodiments, lens 74 may be configured to collect light scattered from the wafer at polar angles from about 20 degrees to about 70 degrees. In addition, lens 74 may be configured as a reflective optical component (not shown) that is configured to collect light scattered from the wafer at azimuthal angles of about 360 degrees.

The inspection system shown in FIG. 3 may also include one or more other channels (not shown). For example, the inspection system may include an additional channel, which may include any of the optical components described herein such as a lens, one or more polarizing components, and a detector, configured as a side channel. The lens, the one or more polarizing components, and the detector may be further configured as described herein. In one such example, the side channel may be configured to collect and detect light that is scattered out of the plane of incidence (e.g., the side channel may include a lens that is centered in a plane that is substantially perpendicular to the plane of incidence and a detector configured to detect light collected by the lens).

The system also includes computer system 80. Output generated by the detectors during each of the scans and during inspection may be provided to computer system 80. For example, the computer system may be coupled to each of the detectors (e.g., by one or more transmission media shown by the dotted lines in FIG. 3, which may include any suitable transmission media known in the art) such that the computer system may receive the output generated by the detectors. The computer system may be coupled to each of the detectors in any suitable manner.

The computer system is configured to detect a population of defects on the wafer using the output generated by each of the two or more scans. The output used to detect the populations of the defects may include output generated by any two or more channels (or detectors) of the inspection system during each of the two or more scans. The computer system may be configured to detect the populations of the defects as described further herein.

The computer system is also configured to identify a subpopulation of the defects for each of the different combinations. Each of the subpopulations includes the defects that are common to at least two of the different combinations. The computer system may be configured to identify the subpopulations of the defects as described further herein. In addition, the computer system is configured to determine a characteristic of a measure of signal-to-noise for each of the subpopulations. The computer system may be configured to determine the characteristic of the measure as described further herein.

The computer system is further configured to select the polarization settings for the illumination and the collection to be used for the inspection of the layer of the wafer corresponding to the subpopulation having the best value for the characteristic. The computer system may be configured to select the polarization settings according to any of the embodiments described herein.

The computer system may be configured to perform any other step(s) of any method embodiment(s) described herein. The computer system may be further configured as described herein. The inspection system may also be further configured as described herein. Furthermore, the system may be further configured as described herein.

It is noted that FIG. 3 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the Puma 9000 and 9100 series of tools that are commercially available from KLA-Tencor, San Jose, Calif. For some such systems, the methods described herein may be provided as optional functionality of the system (e.g., in addition to other functionality of the system). Alternatively, the system described herein may be designed "from scratch" to provide a completely new system.

In some embodiments, a system configured to perform one or more of the computer-implemented methods described herein may include an inspection system such as that described above. However, a system that is configured to perform one or more of the computer-implemented methods described herein may not include an inspection system. For example, the system may include one or more processors or one or more computer systems configured as a stand alone tool. In one such example, the system may include one or more components that are specifically designed (and optionally dedicated) to performing one or more of the computer-implemented methods described herein.

Further modifications and alternative embodiments of various aspects of the invention may be apparent to those skilled in the art in view of this description. For example, computer-implemented methods, carrier media, and systems for selecting polarization settings for an inspection system for inspection of a layer of a wafer are provided. Accordingly, this description is to be construed as illustrative only and is for the purpose of teaching those skilled in the art the general manner of carrying out the invention, It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for selecting polarization settings for an inspection system for inspection of a layer of a wafer, comprising:
    detecting a population of defects on the layer of the wafer using results of each of two or more scans of the wafer performed with different combinations of polarization settings of the inspection system for illumination and collection of light scattered from the wafer;
    identifying a subpopulation of the defects for each of the different combinations, wherein each of the subpopulations comprises the defects that are common to at least two of the different combinations;
    determining a characteristic of a measure of signal-to-noise for each of the subpopulations; and
    selecting the polarization settings for the illumination and the collection to be used for the inspection of the layer of the wafer corresponding to the subpopulation having the best value for the characteristic.

2. The method of claim 1, wherein each of the two or more scans comprises a scan of only a portion of the wafer.

3. The method of claim 1, wherein said detecting comprises applying a single parameter threshold to the results of each of the two or more scans, and wherein the measure of the signal-to-noise comprises results of said applying.

4. The method of claim 1, wherein all steps of the method are performed without knowledge of defects of interest on the wafer.

5. The method of claim 1, wherein all steps of the method are performed without identifying defects of interest on the wafer.

6. The method of claim 1, wherein the defects that are common to the at least two of the different combinations comprise defects that have a higher probability of being salient defects than defects that are not common to the at least two of the different combinations.

7. The method of claim 1, wherein the different combinations comprise all combinations of the polarization settings for the illumination and the collection available on the inspection system.

8. The method of claim 1, wherein the characteristic of the measure of the signal-to-noise comprises an average, and wherein the best value comprises the highest value for the average.

9. The method of claim 1, wherein said selecting comprises selecting one or more polarization settings for the illumination prior to selecting one or more polarization settings for the collection.

10. The method of claim 1, wherein said selecting comprises selecting one or more polarization settings for the illumination and selecting one or more polarization settings for the collection based on the subpopulations corresponding to the one or more polarization settings selected for the illumination.

11. The method of claim 1, wherein said selecting comprises selecting one or more polarization settings for the illumination using a first subset of the subpopulations and selecting one or more polarization settings for the collection using a second subset of the subpopulations.

12. The method of claim 11, wherein the first subset comprises the subpopulations that comprise the defects that are common to the at least two of the different combinations of all of the polarization settings for the illumination and only one of the polarization settings for the collection.

13. The method of claim 11, wherein the second subset comprises the subpopulations that comprise the defects that are common to the at least two of the different combinations of the polarization setting selected for the illumination and all of the polarization settings available for the collection.

14. The method of claim 1, wherein the inspection system comprises one or more illumination channels, and wherein said selecting comprises selecting at least one polarization setting for at least one of the one or more illumination channels.

15. The method of claim 1, wherein the inspection system comprises two or more collection channels, and wherein said selecting comprises selecting the polarization settings for at least two of the two or more collection channels.

16. The method of claim 1, wherein the inspection system comprises more than one collection channel, and wherein said selecting comprises selecting the polarization settings for the collection such that the polarization settings selected for at least two of the more than one collection channel are the same.

17. The method of claim 1, wherein the inspection system comprises more than one collection channel, and wherein said selecting comprises selecting the polarization settings for at least two of the more than one collection channel independently.

18. The method of claim 1, wherein the method is performed for different layers on the wafer.

19. The method of claim 1, wherein all steps of the method are performed without user intervention.

20. A non-transitory carrier medium, comprising program instructions executable on a computer system for performing a computer-implemented method for selecting polarization settings for an inspection system for inspection of a layer of a wafer, wherein the computer-implemented method comprises:
- detecting a population of defects on the layer of the wafer using results of each of two or more scans of the wafer performed with different combinations of polarization settings of the inspection system for illumination and collection of light scattered from the wafer;
- identifying a subpopulation of the defects for each of the different combinations, wherein each of the subpopulations comprises the defects that are common to at least two of the different combinations;
- determining a characteristic of a measure of signal-to-noise for each of the subpopulations; and
- selecting the polarization settings for the illumination and the collection to be used for the inspection of the layer of the wafer corresponding to the subpopulation having the best value for the characteristic.

21. A system configured to select polarization settings for inspection of a layer of a wafer, comprising:
- an inspection system configured to generate output by performing two or more scans of the wafer with different combinations of polarization settings for illumination and collection of light scattered from the wafer; and
- a computer system configured to:
  - detect a population of defects on the wafer using the output generated by each of the two or more scans;
  - identify a subpopulation of the defects for each of the different combinations, wherein each of the subpopulations comprises the defects that are common to at least two of the different to combinations;
  - determine a characteristic of a measure of signal-to-noise for each of the subpopulations; and
  - select the polarization settings for the illumination and the collection to be used for the inspection of the layer of the wafer corresponding to the subpopulation having the best value for the characteristic.

* * * * *